Figure 3:
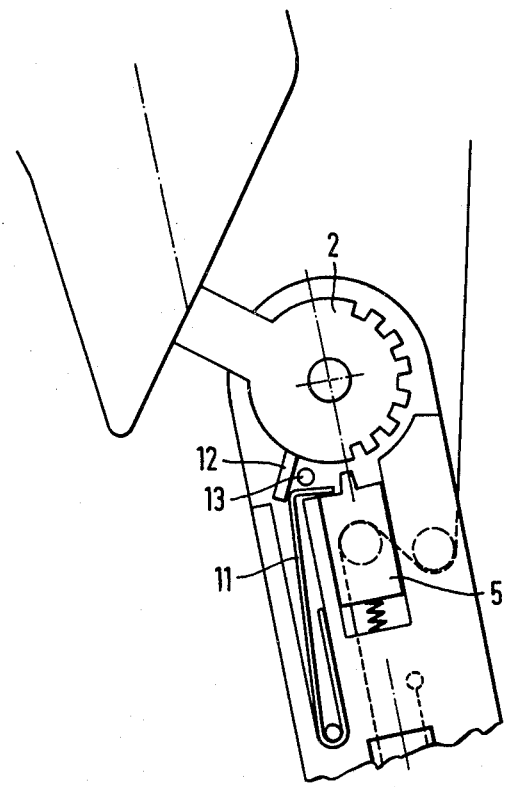

United States Patent [19]
Janovsky

[11] 4,232,405
[45] Nov. 11, 1980

[54] PROSTHESIS JOINT

[75] Inventor: Franz Janovsky, Vienna, Austria

[73] Assignee: Viennatone Gesellschaft m.b.H., Vienna, Austria

[21] Appl. No.: 959,894

[22] Filed: Nov. 13, 1978

[30] Foreign Application Priority Data

Nov. 11, 1977 [AT] Austria .................................. 8101/77

[51] Int. Cl.³ ........................... A61F 1/04; A61F 1/06
[52] U.S. Cl. ............................................. 3/12.3; 3/26
[58] Field of Search .................. 3/12.2, 12.3, 12, 12.1, 3/22, 25–27

[56] References Cited

U.S. PATENT DOCUMENTS

| | | | |
|---|---|---|---|
| 423,840 | 3/1890 | Ulmer et al. | 3/12.2 |
| 1,402,709 | 1/1922 | Blatchford | 3/12.3 X |
| 3,172,127 | 3/1965 | Tolotti | 3/27 |
| 3,382,506 | 5/1968 | Collins et al. | 3/12.3 |
| 4,038,706 | 8/1977 | Ober et al. | 3/12.3 |
| 4,067,070 | 1/1978 | Seamone et al. | 3/12.3 X |

FOREIGN PATENT DOCUMENTS

| | | | |
|---|---|---|---|
| 2119599 | 2/1974 | Fed. Rep. of Germany | 3/12.3 |
| 986866 | 3/1965 | United Kingdom | 3/12.3 |

Primary Examiner—Ronald L. Frinks
Attorney, Agent, or Firm—Kurt Kelman

[57] ABSTRACT

An artificial elbow joint comprises a detent wheel rotatably mounted on the forearm and fixedly connected to the upper arm, the detent wheel having a periphery defining a series of detent notches and a lug affixed thereto and projecting from the periphery. A latch is slidably mounted in relation to the detent wheel and a spring biases the latch against the detent wheel into a first position wherein the tip of the latch engages a respective detent notch to lock the joint. A cable line is attached to the latch and is operable to move it into a second position wherein the latch tip is disengaged and the joint is unlocked, operation of the cable line pivoting the forearm in relation to the upper arm. A leaf spring having an angularly bent end is displaceable between the notched detent wheel periphery and the latch by the lug to retain the latch in the second position.

4 Claims, 4 Drawing Figures

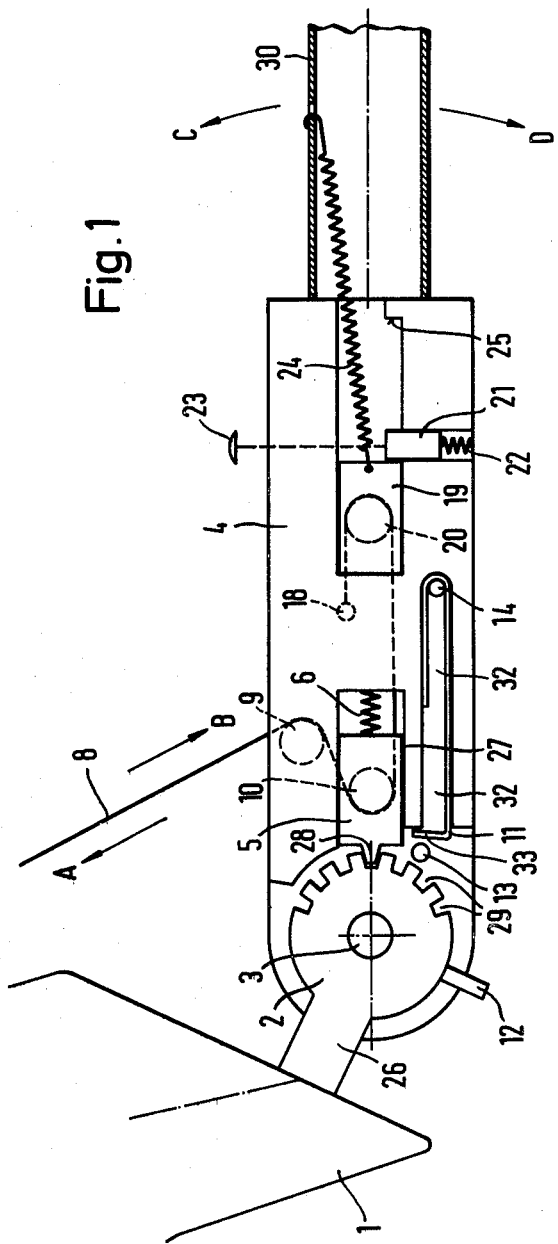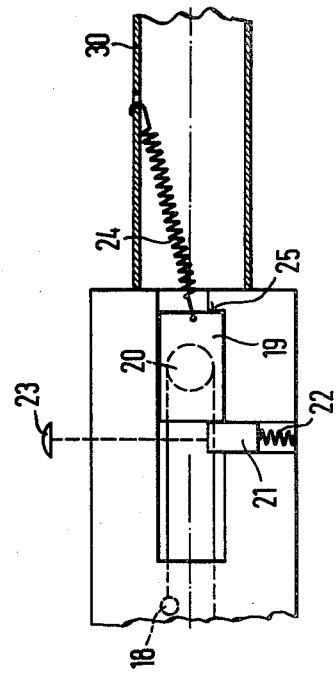

PROSTHESIS JOINT

The invention relates to a prosthesis joint for the rotatable connection of two prosthesis parts, particularly an elbow joint, with a detent body rotatably mounted on one prosthesis part and fixedly connected to the other prosthesis part, the detent body having detent notches on the periphery thereof, wherein the tip of a latch slidable against the detent body under the pressure of a spring may be retained to lock the joint and the latch with the tip is slidable against the pressure of the spring out of the detent notches of the detent body for the purpose of unlocking the detent by a cable line serving to pivot the prosthesis parts in relation to each other.

It is a disadvantage of such prosthesis joints fixed in position by a detent that they are always in the locked position, i.e. with the tip of the bolt retained in a detent notch, when the cable line is not tensioned and a free movement is not possible. This, however, would be desirable, for example, in an artificial elbow joint in an arm prosthesis during walking because the free swinging of the forearm in contrast to a rigid, fixed elbow creates a natural image of motion.

The invention obviates this disadvantage in the above-described prosthesis joint in that the latch may be fixed in a position in which the tip of the latch is located outside the detent notches of the detent body by means of a stop part slidable between the latch and the detent body.

A preferred embodiment of the invention provides that the angularly extending end of a leaf spring is slidable between the detent body and the latch by a lug mounted on the detent body.

Another disadvantage of conventional prosthesis joints actuated by tensile force consists in the fact that a relative long path of the cable line is required before the full bending angle has been reached. When the patient uses the prosthesis sitting at the table, for instance, only a limited bending angle range is primarily required, about from the horizontal position of the forearm to the largest bending height. In this case, a shortening of the cable is advantageous since the patient may then do with a shorter cable line path.

This is accomplished in accordance with the invention by training the cable line between the fixed point and the pulley about a further pulley rotatably affixed to a guide element, the guide element with the other pulley being movable on the latch in a direction away from the pulley after the stop arrangement has been unlatched, preferably by a tension spring.

Figure 4:
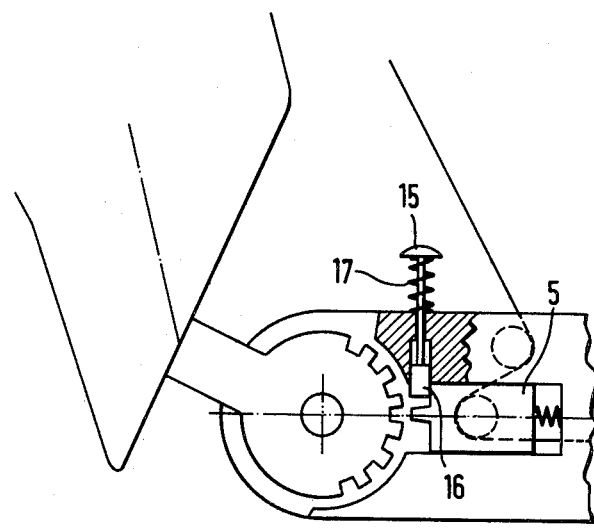

The invention will now be described in more detail with reference to the drawings. In the drawings:

FIG. 1 shows a schematic illustration of an elbow joint according to the invention in bent and locked position, FIG. 2 is a detailed view of the arrangement for shortening the cable line, FIG. 3 is a partial view of the elbow joint of FIG. 1 in its unlatched position, and FIG. 4 shows another embodiment of the arrangement for locking the latch body.

In the elbow joint according to FIG. 1, detent body 2 is affixed to upper arm shaft 1 by means of web 26, the detent body having detent notches 29. Detent body 2 is rotatably mounted in elbow housing 4 affixed to forearm 30 by means of axle 3. Guide 27 is provided in elbow housing 4 and latch 5 with detent tip 28 is pressed in the guide against detent body 2 by means of compression spring 6. When detent tip 28 of latch 5 is retained in a notch 29 of detent body 2, the elbow joint is locked, i.e. the position between upper arm 1 and forearm 30 is fixed. A respective pulley 9, 10, 20 is rotatably mounted in elbow housing 4, latch 5 and guide 19 displaceable in guide 27. Cable 8 is trained over the three pulleys 9, 10 and 20 and is fastened to the elbow joint at a fixed point 18. If the cable is pulled in the direction of arrow A, latch 5 is moved against the pressure of spring 6 and this causes detent tip 28 to be moved out of detent notch 29. Upon further movement of cable 8 in the direction of arrow A after latch 5 has reached its end position, forearm 30 is pivoted against the force of gravity in the direction of arrow C about axle 3. However, forearm 30 pivots under the force of gravity in the direction of arrow D as soon as cable 8 is slowly and constantly released in the direction of arrow B.

When cable 8 is suddenly released—while forearm 30 is only slowly set into motion due to its considerable mass inertia, spring 6 can move latch 5 into a notch 29 of detent body 2.

In this manner, the elbow joint is locked in the desired position.

The arrangement for maintaining an unlocked position consists of leaf spring 11 and lug 12 affixed to detent wheel 2. Leaf spring 11 is positioned under tension in slot 32 of elbow housing 4 and is held by pin 14. When forearm 30 is brought to its maximum stretch position so that lug 12 on detent wheel 2 engages stop pin 13 in elbow housing 4, bent end 33 of leaf spring 11 is guided simultaneously in front of the face of the latch under the tip (see FIG. 3). This prevents the latch from being pressed against detent wheel 2 after the tensile force has ceased and from locking the joint. Therefore, the arm may swing freely in this position. Since leaf spring 11 is prevented from returning to its initial position because of the frictional engagement of bent end 33 with latch 5, the elbow joint remains unlocked even when pin 12 no longer presses against leaf spring 11 during the free swinging of the forearm. Only a renewed pulling on cable 8 causes latch 5 to be displaced so that it no longer presses against angularly bent end 33 of leaf spring 11 and the latter returns to the position illustrated in FIG. 1, due to its pre-tension. In this position, the elbow joint may be locked again.

FIG. 4 shows another embodiment of a free swinging arrangement. In this embodiment,—with latch 5 in the retracted position—pin 16 is guided in front of the face above the tip of the latch by depressing button 15 and is prevented from gliding back after the tensile force has ceased by friction force. Only renewed pulling on the cable until the friction force has been overcome permits the pin to glide upwardly under the pressure of compression spring 17 so that the latch is capable of funtioning.

An arrangement for shortening the cable line is illustrated in FIGS. 1 and 2. Cable 8, which is fastened to elbow housing 4 at point 18, is trained over pulley 20 mounted on guide element 19. Guide element 19 is movably mounted in the elbow housing but is retained in the position shown in FIG. 1 by stop 21 despite the tensile force exerted by tension spring 24.

Button 23 is rigidly connected to stop 21. Depressing of the botton frees guide element 19 and—as long as the cable is free of tension—pulls it by tension spring 24 until it engages abutment face 25. Under the pressure of compression spring 22, stop 21 returns into its initial position. Guide element 19 is now retained between stop 21 and abutment face 25, which amounts to shortening the cable by twice the displacement path of guide element 19 (see FIG. 2).

The shortening of the cable can be removed again by pulling the cable and simultaneously depressing button 23 if button 23 is released again after guide element 19 has been retracted into its initial position (FIG. 1).

I claim:

1. A prosthesis joint for the rotatable connection of two prosthesis parts pivotal in relation to each other, which comprises
    (a) a detent body rotatably mounted on one of the prosthesis parts and fixedly connected to the other prosthesis part, the detent body having a periphery defining a series of detent notches and a lug affixed thereto and projecting from the periphery,
    (b) a latch having a tip, the latch being mounted slidably in relation to the detent body,
    (c) a spring biasing the latch against the detent body into a first position wherein the tip of the latch engages a respective one of the detent notches to lock the joint,
    (d) a cable line attached to the latch and operable to move the latch against the spring bias into a second position wherein the tip of the latch is disengaged from the one detent notch to unlock the joint, operation of the cable line pivoting the one prosthesis part in relation to the other prosthesis part, and
    (e) a stop part including a leaf spring having an angularly bent end displaceable between the notched periphery of the detent body and the latch by the lug to retain the latch in the second position.

2. The prosthesis joint of claim 1, further comprising a stop pin mounted between the lug and the latch, the lug being arranged to engage the stop pin in the second position of the latch.

3. The prosthesis joint of claim 1 or 2, further comprising a guide element slidable in tandem with the latch into first and second positions, the cable line having one end affixed to the one prosthesis part, respective pulleys rotatably mounted on the latch and on the guide element, the cable line being trained from the one end over the pulley mounted on the guide element and subsequently over the pulley mounted on the latch, and a stop arrangement mounted to latch the guide element in the first position and to unlatch the guide element to permit its movement into the second position.

4. The prosthesis joint of claim 3, further comprising a tension spring for unlatching the stop arrangement.

* * * * *